United States Patent [19]
Potratz et al.

[11] Patent Number: 5,921,921
[45] Date of Patent: Jul. 13, 1999

[54] PULSE OXIMETER WITH SIGMA-DELTA CONVERTER

[75] Inventors: Robert Stephen Potratz, Overland Park, Kans.; Michael W. Nootbaar, Benica, Calif.

[73] Assignee: Nellcor Puritan-Bennett, Pleasanton, Calif.

[21] Appl. No.: 08/769,148

[22] Filed: Dec. 18, 1996

[51] Int. Cl.$^6$ .................................................. A61B 5/00
[52] U.S. Cl. .................................................. 600/323
[58] Field of Search ................................... 600/322, 323, 600/330, 324, 336; 356/41; 341/143

[56] References Cited

U.S. PATENT DOCUMENTS

| | | |
|---|---|---|
| 4,621,643 | 11/1986 | New, Jr. et al. . |
| 4,700,708 | 10/1987 | New, Jr. et al. . |
| 4,770,179 | 9/1988 | New, Jr. et al. . |
| 4,802,486 | 2/1989 | Goodman et al. . |
| 4,830,014 | 5/1989 | Goodman et al. . |
| 4,869,254 | 9/1989 | Stone et al. . |
| 4,892,101 | 1/1990 | Cheung et al. ........................ 600/324 |
| 4,911,167 | 3/1990 | Corenman et al. . |
| 4,928,692 | 5/1990 | Goodman et al. . |
| 4,934,372 | 6/1990 | Corenman et al. . |
| 5,078,136 | 1/1992 | Stone et al. . |
| 5,190,038 | 3/1993 | Polson et al. .......................... 600/330 |
| 5,337,230 | 8/1994 | Baumgartner et al. ................. 600/508 |
| 5,348,004 | 9/1994 | Hollub ................................... 600/330 |
| 5,351,685 | 10/1994 | Potratz . |
| 5,368,026 | 11/1994 | Swedlow et al. . |
| 5,471,209 | 11/1995 | Sutterlin et al. ....................... 341/143 |
| 5,533,507 | 7/1996 | Potratz . |

*Primary Examiner*—Cary O'Connor
*Assistant Examiner*—Eric F. Winakur
*Attorney, Agent, or Firm*—Hovey, Williams, Timmons & Collins

[57] ABSTRACT

A preferred oximeter detects the transillumination by red and infrared light of a portion of an in vivo subject and produces analog signals representative thereof on two channels. Sigma-delta modulators sample the analog signals on each channel. A digital filter processor digitally filters the sample signals from both modulators to produce respective digital signals with multi-bit resolution.

55 Claims, 5 Drawing Sheets

Microfiche Appendix Included
(1 Microfiche, 54 Pages)

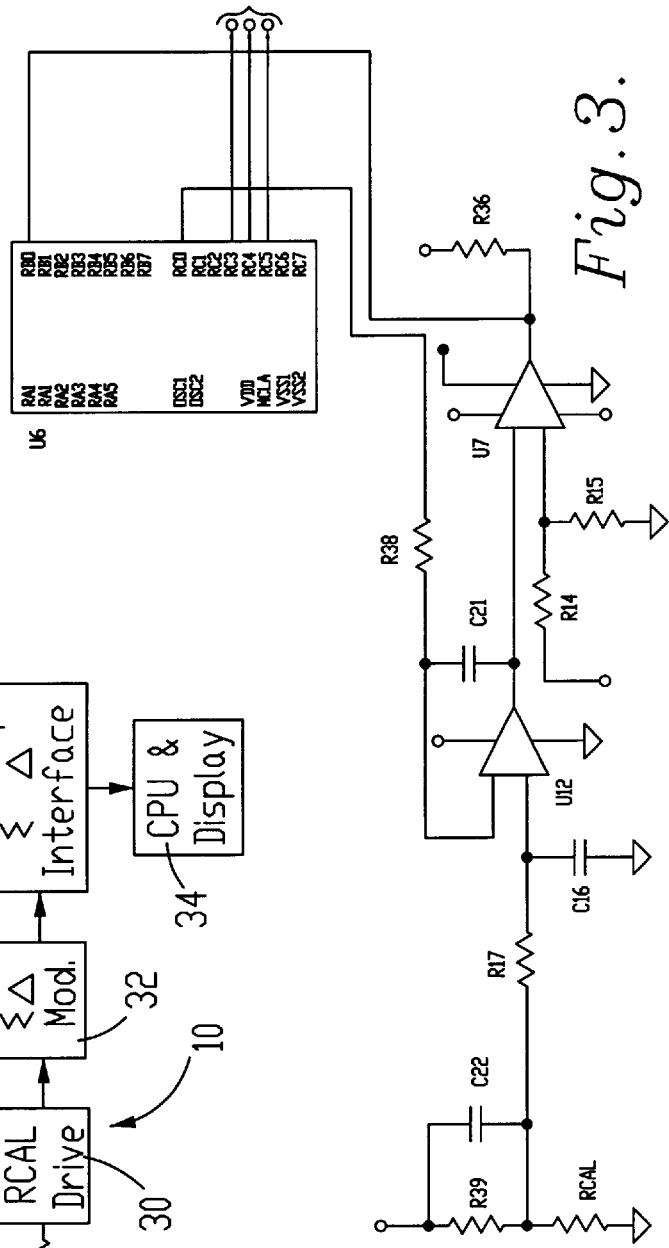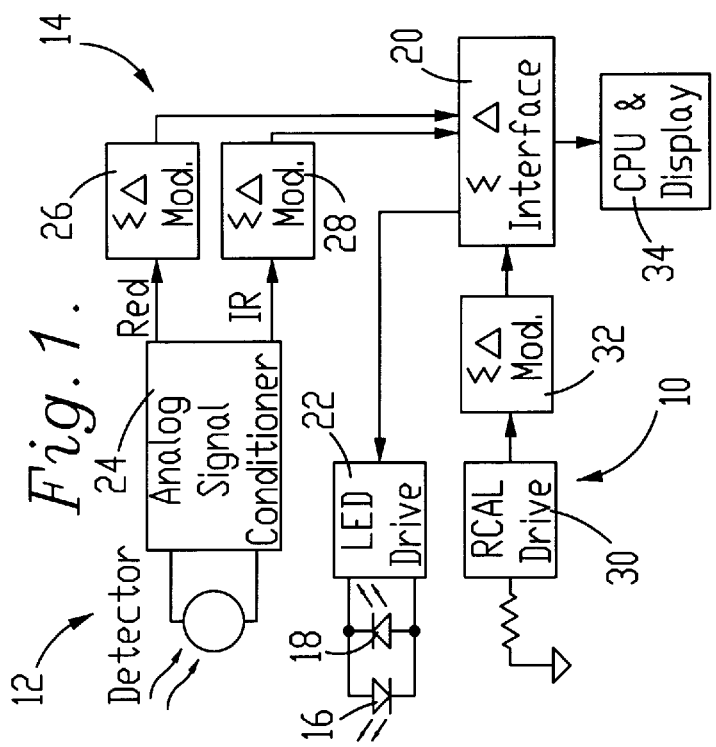

PULSE OXIMETER WITH SIGMA-DELTA CONVERTER

RELATED APPLICATIONS

Not applicable.

FEDERALLY SPONSORED RESEARCH OR DEVELOPMENT

Not applicable.

MICROFICHE APPENDIX

A microfiche appendix containing a source code of a computer program useful in accordance with the present invention is appended hereto as 1 sheet of micro-fiche containing 54 frames incorporated as part of the disclosure hereof.

BACKGROUND OF THE INVENTION

1. Field of the Invention

The present invention relates to the field of oximeters for determining the oxygen saturation in the blood of a subject. More particularly, the invention is concerned with an oximeter using sigma-delta analog to digital converters.

2. Description of the Prior Art

Prior art oximeters detect the transillumination by red and infrared light of a body portion of an in vivo subject in order to determine the blood oxygen saturation of the subject. Analog detector signals representative of the transillumination are converted to digital signals and then processed to determine blood oxygen saturation. The digital signals need to present high resolution in order to provide sufficient accuracy. Typically, conventional analog to digital converters have been used such as sample and hold converters. A converter is needed for each red and infrared channel and for the calibration channel. The use of three converters represents substantial cost and adds to the size of the circuitry.

Other prior art oximeters have used an off-the-shelf converter chip for each channel that includes a sigma-delta modulator and digital filtering on the same chip. This still requires the use of three converters and does not allow flexibility in selecting digital signal resolution.

SUMMARY OF THE INVENTION

The present invention solves the prior art problems discussed above and provides a distinct advance in the state of the art. More particularly, the oximeter hereof eliminates the need for separate analog to digital converters for each channel thereby reducing the cost, complexity and size of the circuitry.

The preferred oximeter includes a probe for producing and detecting transillumination, including transmittance and reflectance, of a body portion of in vivo subject by two wavelengths of radiation preferably red and infrared light and for producing analog signals representative thereof, converter circuitry for converting the analog signals to digital signals, and a signal processor for processing the digital signals in order to determine blood oxygen saturation of the subject. The converter circuitry includes a sigma-delta modulator for each of the red and infrared channels for producing respective sample signals, and a single digital filter processor for receiving the sample signals from both modulators and for producing the respective digital signals. The preferred oximeter also includes a sigma-delta modulator for the calibration channel and the digital filter processor handles the signals from this modulator as well.

BRIEF DESCRIPTION OF THE DRAWINGS

FIG. 1 is an electrical block diagram illustrating the preferred oximeter of the present invention;

FIG. 3 is an electrical schematic of the RCAL drive, RCAL sigma-delta modulator and interface of FIG. 1;

DETAILED DESCRIPTION OF THE PREFERRED EMBODIMENT

Figure 2A:
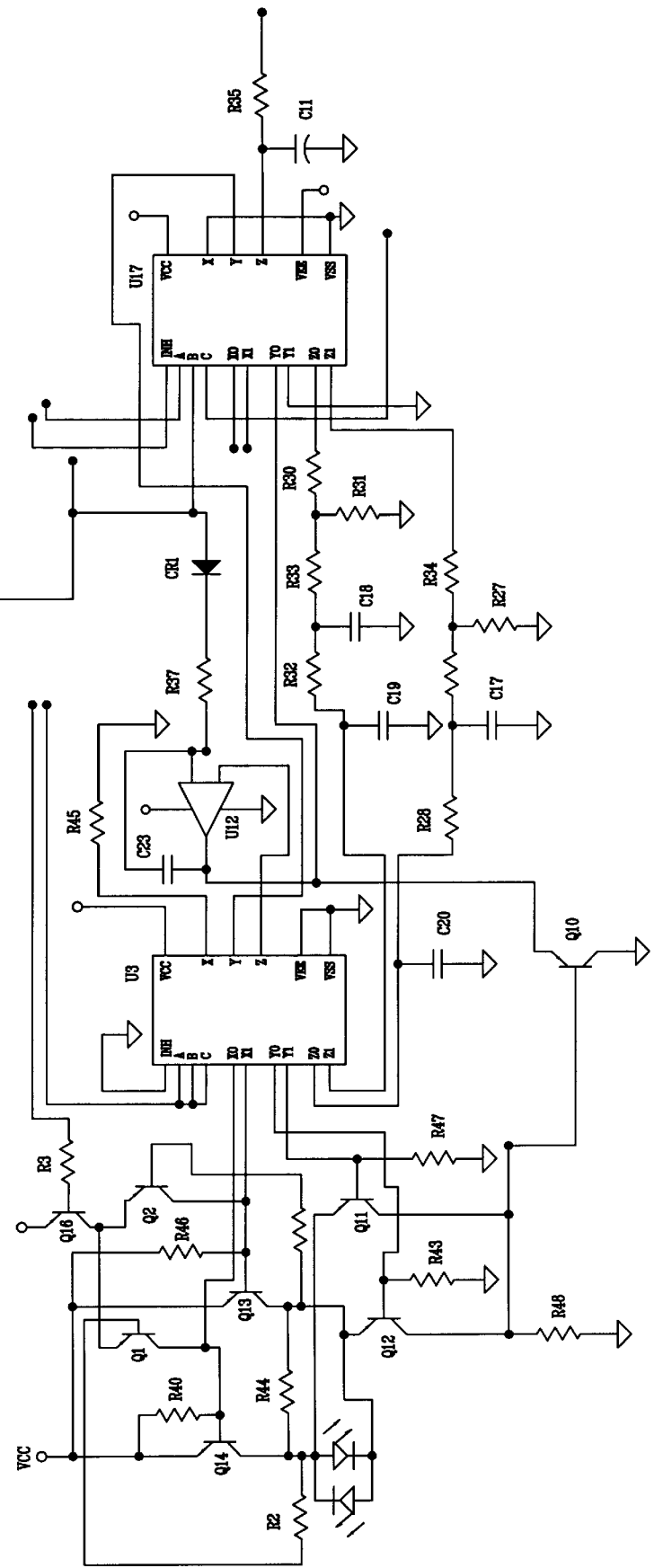
FIG. 2A is an electrical schematic of the interface, LED drive and LED's of FIG. 1.

FIG. 1 is an electrical block diagram illustrating the preferred oximeter 10 of the present invention. Oximeter 10 includes probe 12 and oximeter circuitry 14. Probe 12 is configured for attaching to a subject's body portion such as a finger and includes red light emitting diode (LED) 16, infrared LED 18, detector 19 and a calibration resistor designated RCAL. The preferred probe 12 is described in U.S. Pat. Nos. 4,770,179, 4,621,643, 4,700,708 and 4,830,014, the disclosures of which are hereby incorporated by reference.

Oximeter circuitry 14 includes interface 20, LED drive 22, analog signal conditioning circuit 24, red channel sigma-delta modulator 26, infrared channel sigma-delta modulator 28, RCAL drive 30 and RCAL sigma-delta modulator 32. Circuitry 14 further includes central processing unit (CPU) 34 that receives from interface 20 multibit resolution signals representative of the transmittance of red and infrared light from LED 16, 18 to detector 20 through the subject's body portion. From this information, CPU 34 then determines the blood oxygen saturation of the subject in the manner described in U.S. Pat. Nos. 5,533,507 and 5,351,685, the disclosures of which are hereby incorporated by reference. The present invention is concerned with a method and apparatus for providing the needed signals to CPU 34.

LED DRIVE

Figure 2B:
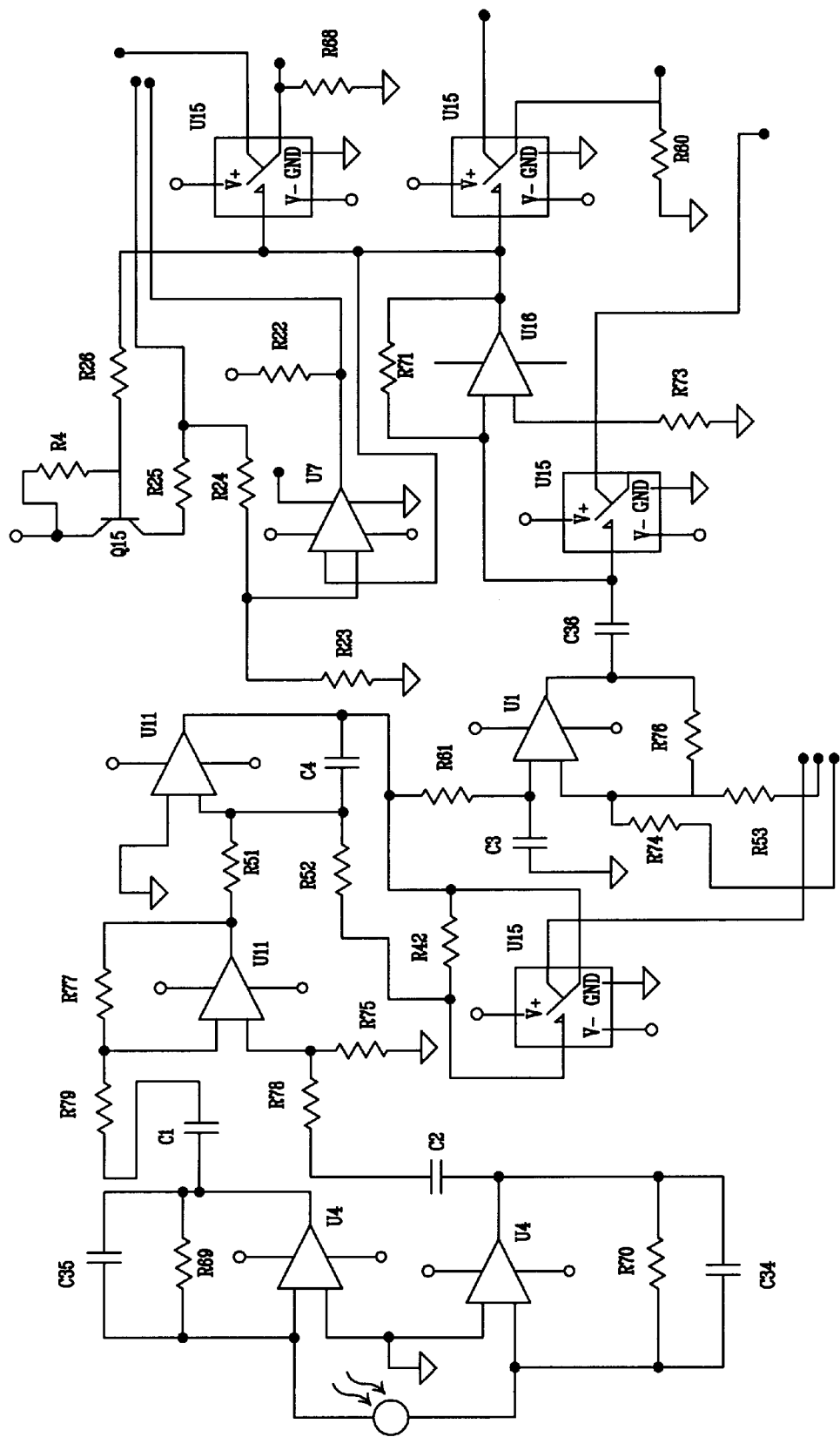
FIG. 2B is an electrical schematic of the interface, analog signal conditioning circuit and detector of FIG. 1.
Figure 2C:
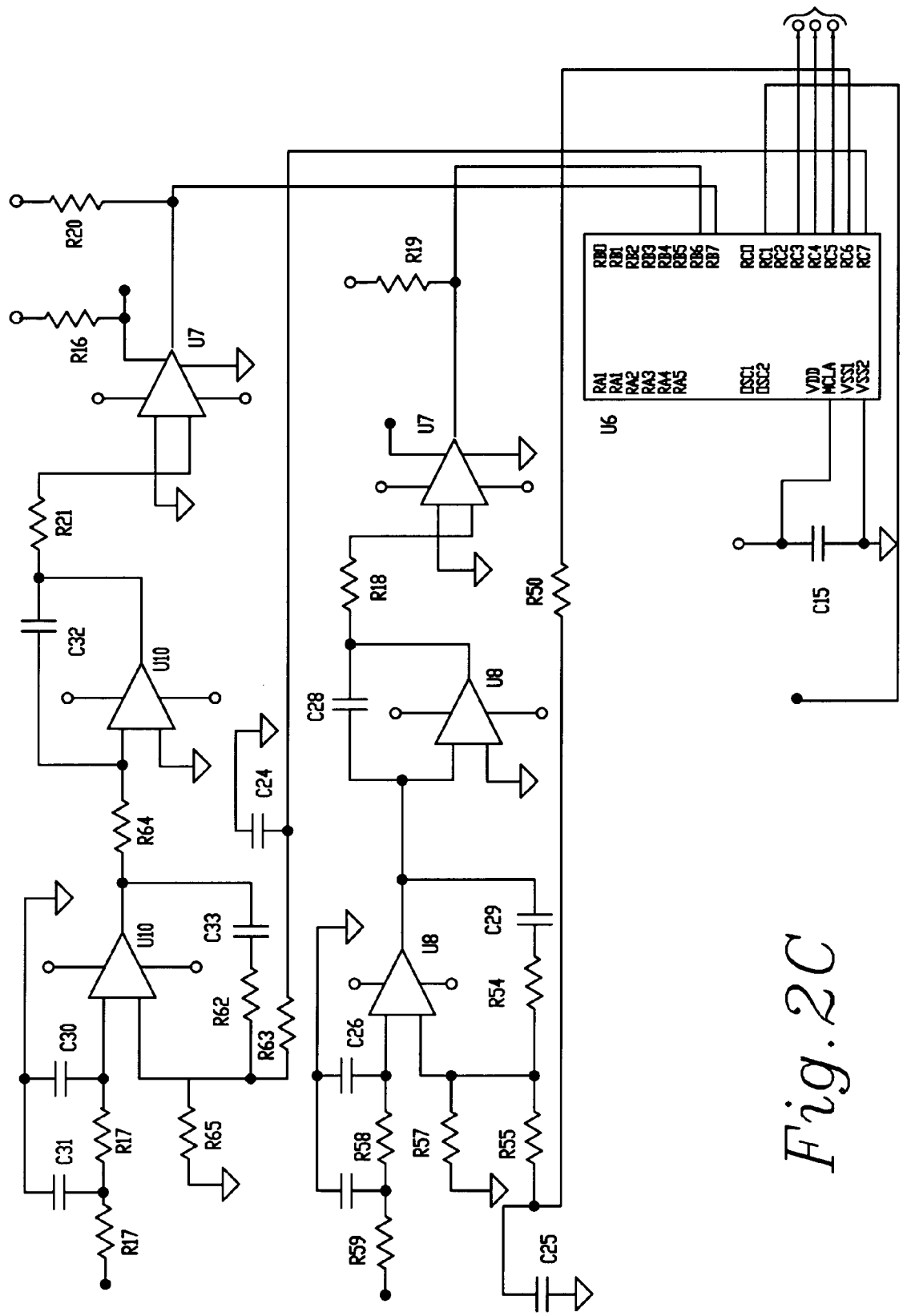
FIG. 2C is an electrical schematic of the interface and red and infrared channel sigma-delta modulators of FIG. 1.

FIG. 2A is an electrical diagram illustrating LED's 16,18, interface 20, LED drive 22 and the connections therebetween. Interface 20 is preferably a microprocessor (type PIC16C63) under control of the program shown in the microfiche appendix incorporated as part of the disclosure hereof. Interface 20 is also connected with other components. These other components and connections are illustrated in FIGS. 2B and 2C. In general, inputs to interface 20 are received at terminals RB0–RB7 and outputs are provided at terminals RC0–RC7 and RA0–RA5. In addition to the components illustrated, a conventional 10 MHZ oscillator is connected to terminals 9 and 10.

In general, interface 20 controls the operation of LED drive 22 in order to alternately activate LED's 16,18 and to control individually the intensities of LED's 16,18 when activated. The control is designed so that the signals received by detector 20 and provided to circuit 24 are in the desired range for optimal sensitivity and resolution.

In operation, interface 20 provides a first pulse width modulated (PWM) signal from terminal RC1. The pulse width of this signal represents the level of maximum intensity of LED's 16,18. The PWM signal is filtered and smoothed by R35 (10K) and capacitor C11 (0.47 uF) to produce a D.C. voltage corresponding to the duty cycle of the PWM signal as a drive reference to terminal Z of switch U17 (type CD40536).

Interface 20 provides a second PWM signal from terminal RC2 to U17 terminal C. This second PWM signal determines the relative intensities of LED's 16,18. With a logic low signal at terminal C, terminal Z is connected to Z0 which also provides the drive reference voltage to Z0. However, a logic high signal at terminal C disconnects Z from Z0. Thus, the output from terminal Z0 is a square wave having a maximum voltage equal to the drive reference on terminal Z and having a duty cycle according to the second PWM signal on terminal C. This is the reference signal for the intensity of red LED 16 and is filtered and smoothed by resistors R30 (80.6K), R31 (11K), R33 (174K) and R32 (174K) along with capacitors C18 (0.1 uF), C19 (0.1 uF) and C20 (0.1 uF) connected as shown. The resulting D.C. voltage is supplied as the red reference to terminal Z1 of switch U3 (type CD4053S).

The output from terminal Z1 of switch U17 is a square wave with a duty cycle complementary to that on Z0. For example, if the duty cycle on Z0 is 75%, then the duty cycle on Z1 would be 25%. The output from Z1 is provided to switch U3 at terminal Z0 as the infrared (IR) reference voltage. Filtering and smoothing are provided by resistors R34 (80.6K), R27 (10K), R29 (174K) and R28 (174K) and capacitors C17 (0.1 uF) and C20 (0.1 uF).

As will be appreciated, the duty cycle on U17 terminal C controls the ratio of the intensities on LED's 16,18. Moreover, very fine control of LED intensity is possible because 256 counts of resolution are available for the drive reference at terminal Z and a further 256 counts resolution are available at terminal C with regard to the intensity duty cycle. Such precision has not been possible with prior art oximeters.

Switch U3 controls the alternating activation of LED's 16,18 in response to control signals received at terminals A, B and C from interface 20 terminal RA3. This control signal is a 50% duty cycle signal at twice the frequency of LED illumination. In other words, each LED is activated for only the initial half of its cycle and off during the second half to provide a quiescent time for zeroing in analog signal conditioning circuit 24.

With U3 terminals A, B and C logic low, IR reference voltage at Zo is connected to terminal Z and from there to the noninverting input (pin 3) of comparator U12. Capacitor C23 (4.7 pF) provides feedback between the output of comparator U12 and the inverting input (pin 4). This comparator controls current flow through LED's 16,18 in accordance with the reference signal provided on pin 3.

The output from comparator U12 is connected to switch U17 terminal Y0 and, on the IR part of the cycle, to terminal Y and from there to switch U3 terminal Y. With switch U3 terminal B logic low, terminal Y is connected to terminal Y0 and from there to the base of transistor Q12 (type MPSA06S). This transistor controls the current flow through IR LED 18 and through resistor R48 (10.0) to ground. Resistor R33 (10K) provides pull down to the base of Q12. The current through resistor R48 produces a representative voltage provided by way of resistor R41 (22.1K) as feedback to the inverting input of comparator U12. Interface 20 terminal RA2 provides a control signal by way of diode CR1 (IN9149) and resistor R37 (100K) to the inverting input of comparator U12. A high signal from interface 20 turns off U12 which in turn provides redundant turn off for the LED's. By so doing, current surges through the LED's are avoided during turn on which in turn eliminates a source of interference to the detector signals.

The logic low signal at switch U3 terminal B connects ground at terminal X by way of resistor R45 (3.32K) to terminal X0 and from there to the base of transistor Q14 (type MPSA56S). This low signal turns on transistor Q14 to provide supply voltage to the anode of IR LED 18. Resistor R40 (10K) interconnects the base and emitter of transistor Q14.

When it is time to activate red LED 16, interface 20 produces a logic high signal at switch U3 terminals A, B and C. This connects terminal Z1 to Z to provide red reference voltage to comparator U12. The logic high signal disconnects X0 from X allowing the base voltage on transistor Q14 to rise turning off this supply, but allowing the voltage to rise on the base of transistor Q13 (type MPSA56S) by way of resistor R46 (10K). Transistor Q13 provides supply voltage to the anode of red LED 16.

The logic high signal to switch U3 terminal B disconnects Y0 from Y turning off transistor Q12 and connects terminal Y to Y1 and from there to the base of transistor Q11 (type MPSA06S). Transistor Q11 turns on and begins to conduct through red LED 16 and resistor R48. Resistor R40 (10K) provides pull down to the base of transistor Q11.

LED drive 22 also includes a protection subcircuit for preventing excess current flow through LED's 16,18 in the event of a shorted lead of probe 12. The protection subcircuit includes transistors Q1, Q2 and Q16 (all type 2N3906S). Transistor Q16 enables the protection subcircuit by providing supply voltage to transistors Q1 and Q2 in response to a logic low signal from interface 20 terminal RB2 by way of resistor R3 (20K) to the base of transistor Q16. During normal operation, transistor Q16 is activated but can be turned off during testing.

A short to ground on the cathode of IR LED 18, for example, causes the current flow to bypass transistor Q12 and resistor R48 leading to excess current flow through the LED. This can cause excessive heat. If this occurs, the base of transistor Q2 is pulled down to the ground fault through resistors R1 (20K) and R44 (20K). When this occurs, transistor Q2 turns on supplying base current to transistor Q13 which then turns off, thereby interrupting supply voltage to IR LED 18. Similarly, if the fault is on the cathode of red LED 16, the base of transistor Q1 is pulled down through resistors R44 and R2 (20K) which supplies base current to turn off transistor Q14 and interrupts supply voltage to LED 18.

ANALOG SIGNAL CONDITIONING CIRCUIT

Detector 19 receives and detects light from LED's 16,18. This detected light represents the absorption by the subject of the two frequencies of light which in turn represents the blood oxygen level of the subject. Analog signal conditioning circuit 24 filters and amplifies the analog signal from detector 20 and further separates the signal into red and IR channels presented to sigma-delta modulators 26 and 28.

Detector 19 is connected between the inverting terminals (pins 2 and 6) of two halves of operational amplifier U4 (type AD822). The noninverting terminals (pins 3 and 5) are connected to ground which produces a virtual ground on the inverting terminals. Resistor R69 (249K) and capacitor C35 (100 pF) are connected in parallel between the noninverting input and the output of the first half. Similarly, resistor R70 (249K) and capacitor C34 (100 pF) are connected across the noninverting input and the output of the second half. With this configuration, the output from the first half is a positive voltage signal proportional to the current through detector 20, and the output from the second half is a negative voltage signal proportional to the current through detector 20.

Circuit 24 provides two stages of gain with each stage providing a gain of up to 16 for a total possible gain of 256. The outputs from amplifier U4 are presented to the first stage. In particular, the positive voltage signal is AC coupled by way of capacitor C1 (0.1 uF) and resistor R79 (49.9K) to the inverting terminal (pin 8) of differential amplifier U11 (type LT1013S). Similarly, the negative voltage signal is AC coupled by way of capacitor C2 (0.1 uF) and resistor R78 (49.9K) with the noninverting input (pin 1) of amplifier U11. Resistor R77 (49.9K) provides feedback from the output of amplifier U11 to the inverting input. The AC coupling filters the DC components from the voltage signals and the output from amplifier U11 is an AC signal with one portion representing red light and the other portion representing IR light received by detector 20.

The output (pin 7) for the first half of amplifier U11 is provided by way of resistor R51 (49.9K) to the inverting input (pin 4) of the other half of amplifier U11. The noninverting input is connected to the ground. The gain of this stage is determined by the feedback from the amplifier output (pin 5) to the noninverting input (pin 4) and is selectable between a gain of 0.5 and 8 for a gain range of 16. Specifically, capacitor C4 (47 pF) is connected between pins 4 and 5 as are series connected resistors R52 (24.9K) and resistor R42 (374K). These two resistors provide a gain of 8. However, switch U15 bypasses resistor R42 upon receipt of a logic high signal from interface 20 terminal RB3 in order to select a gain of 0.5. The software in interface 20 selects the gain as needed in order to keep signal levels in the optimal range for accuracy.

The output from amplifier U11 (pin 5) is provided by way of resistor R61 (12.1K) to the second stage and in particular, to amplifier U1 noninverting input pin 1. Capacitor C3 (4700 pF) is also connected to this input and together with resistor R61 provides signal filtering. Resistor R76 (374K) is connected between the output (pin 7) and the inverted input (pin 8) of amplifier U1.

Additionally, resistors R74 (12.1K) and R53 (374K) are connected to the inverting terminal with the other sides connected to switch U17 terminals X1 and X0 respectively. Under control of interface U20, either of terminals X0 or X1 are connected to ground through terminal X to connect resistor R53 or R74. This selects the gain of this stage as either 2 or 32.

The output from amplifier U1 is connected by way of capacitor C6 (0.1 uF) and resistor R72 (100K) to the inverting input of amplifier U16. This output is also connected by way of capacitor C36 to switch U15. The noninverting input of amplifier U16 is connected to the other side of switch U15 and also to one side of resistor R73 (100K). Resistor R71 (100K) interconnects U16 output pin 7 and pin 6. Under the control of interface 20, switch U15 closes during the quiescent period between activations of LED's 16,18 in order to eliminate the effects of ambient light and other noise sources on detector 20.

The output (pin 7) from amplifier U16 is connected to the next stage for demultiplexing the signal, that is, for separating the signal into red and IR channels. Specifically, the output from amplifier U16 is connected to red channel switch U15 pin 15 and IR channel switch U15 pin 2. Switch U15 pin 14 is connected to ground by way of resistor R28 (10K) and pin 3 is connected to ground by way of resistor R60 (10K). When red LED 16 is activated, interface 20 activates terminal RA0 at logic high to close the switch between U15 pins 15 and 14 in order to provide the red channel signal to sigma-delta modulator 26. Similarly, when IR LED 18 is activated, interface 20 activates terminal RA1 at logic high to close the switch between U15 pins 2 and 3 in order to provide the IR channel signal to sigma-delta modulator 28.

Comparator U7 compares the output from U16 with a reference voltage on resistor R23 (1.62K) which is part of a voltage divider including series connected resistors R24 and R25 (24.9K each) and transistor Q15 (type 2N3906S) with the emitter connected to a voltage source at 10 volts. Resistor R4 (49.9K) interconnects the base and emitter of Q15 and resistor R26 (49.9K) interconnects the base of Q15 with the output of Q16.

The output from U7 is connected to interface 20, terminal RB4 and indicates whether the output from U16 is above the reference on R23. If yes, then interface 20 does not switch in additional gain which would saturate the amplification. If no, the additional gain is added. A high output from U16 to the base of Q15 shuts off this transistor which in turn reduces the reference voltage to U7 to zero. As a result, the output from U7 is zero to interface 20 indicating that the gain is too high. Interface 20 responds by reducing the gain.

RED AND IR CHANNEL SIGMA-DELTA MODULATORS

Sigma-delta modulators 26,28 are identical in structure and operation as illustrated in FIG. 2C. Accordingly, only the operation of red channel modulator 26 is discussed in detail. Modulator 26 provides two stages of integration. Specifically, the red channel analog signal from conditioning circuit 24 is received by way of resistors R67 (174K) and R66 (174K) at the noninverting terminal (pin 3) of integrator U10 (type LT1013S). Capacitors C31 (0.1 uF) and C30 (0.1 uF) are connected as shown and cooperate with resistors R66 and R67 to provide input filtering. Series coupled capacitor C33 (0.1 uF) and resistor R62 (49.9K) interconnect the output of U10 and the inverting input (pin 4), which is also connected to ground by way of resistor R65 (49.9K).

The output from amplifier U10 (pin 5) is connected by way of resistor R64 (100K) to second stage integrator U10 (type LT1013S) inverting terminal (pin 8). Capacitor C32 (0.01 uF) interconnects the output (pin 7) of U10 with pin 8. The noninverting terminal is connected to ground.

The output from integrator U10 is provided by way of resistor R21 (10K) to the inverting terminal of comparator U7 (type LP365S) with the noninverting terminal connected to ground. Bias current is provided by way of resistor R16 (1.8M) and reference voltage is provided to the output (pin 14) of U7 by way of resistor R20 (10K). The output from comparator U7 is provided to interface 20 at terminal RB7. The comparator output is a digital signal with a duty cycle representing the red channel analog signal voltage level.

In operation, interface 20 generates feedback for the modulator process by providing the comparator output at terminal RB7 as output on terminal RC7. This feedback is provided from terminal RC7 by way of resistor R49 (150K) and resistor R63 (200K) to the inverting terminal (pin 4) of integrator U10, as is conventional.

However, in the present invention, interface 20 selects the duty cycle of the feedback on terminal RC7 in order to select the gain through sigma-delta modulator 26 as a programmable gain. More particularly, the sampling rate at interface 20 terminal RB7 is 4.883 KHz. With a clock speed of 10 MHZ, this provides a maximum sample time of 512 cycles. The software controls the number of cycles that feedback is provided on terminal RC7 and thereby controls the gain through modulator 26. For example, by providing gain for 256 of the 512 cycles, modulator 26 provides a gain of 2. The gain is selected to provide the optimal range depending upon the level of the signal. For example, if the red channel analog signal is weak, the gain through modulator 26 is increased.

Interface 20 performs digital signal filtering of the digital signal received at terminal RB7 from modulator 26. In particular, the software performs divide-by-64 decimation filtering by performing six stages of divide-by-2 decimation filtering. This results in 78 samples per second as the update rate. The output from the decimation filtering is then filtered by a fourth order Bessel filter resulting in an output digital signal representative of the red channel analog signal with a resolution of at least 17 bits and a bandwidth of 5 Hz updated 78 times per second. The result is a red output digital signal provided to CPU 34. Modulator 28 performs the same conversion as modulator 26 but for the IR channel analog signal and interface 20 performs the same filtering in order to provide an IR output digital signal to CPU 34.

In the preferred embodiment, the parameters of sampling rate, filter cutoff and update rate are controlled by the programming in interface 20. By doing so, these parameters can be selected as needed for optimal performance in a given application. That is, control of these parameters in software provides flexibility and ease of changes. In the prior art, these parameters have been designed in hardware, which does not allow for flexibility or changes.

RCAL DRIVE AND SIGMA-DELTA CONVERSION

RCAL drive 30 illustrated in FIG. 3 includes resistor R39 (10K) and parallel coupled capacitor C22 (0.1 uF). Resistor R39 is coupled in series with resistor RCAL as a voltage divider network between reference voltage and ground. The voltage across at least one RCAL resistor is proportional to the resistance value and can be readily determined with the reference voltage being known, preferably utilizing encoded, preselected information indicative of at least one LED wavelength, e.g., calibration information which is correlated with resistance. Thus, the RCAL voltage signal, as an analog encoded signal, is representative of the resistance and is provided by way of resistor R17 (174K) and capacitor C18 (0.1 uF), connected as shown in FIG. 3, which provide signal filtering. The filtered RCAL analog signal is then provided to RCAL sigma-delta modulator 32.

Sigma-delta modulator 32 includes a one stage integrator U12 (type LT1013S) and comparator U7 (type LP365S). Integrator U12 receives the filter RCAL analog signal at the noninverting input (pin 1) and provides an output on pin 7 to comparator noninverting input pin 8. Capacitor C21 (0.033 uF) interconnects the U12 output (pin 7) with the inverting input (pin 8) of comparator U7. Reference voltage is provided to the inverting input of U7 by way of resistor R14 and resistor R15 (10K) connects the inverting input to ground. Reference voltage is provided to the output (pin 2) of U7 by way of resistor R36 (10K).

The output from U7 is a digital signal, as a third sample signal, representative of the RCAL analog signal and is provided to interface 20 terminal RB0. Interface 20 provides sigma-delta feedback from terminal RC0 by way of resistor R38 (100K) to the inverting input of integrator U12. Interface 20 then performs conventional digital filtering to produce a digital signal output with multibit resolution, preferably of 17-bit resolution, as a digital encoded signal, to CPU 34, which processes the signal in the manner described in U.S. Pat. No. 4,770,179 previously hereby incorporated by reference.

In another aspect of the present invention, it will be recognized by those skilled in the art that certain combinations of circuit functions can be adapted to application specific integrated circuit (ASIC) embodiments. As an example of such an ASIC embodiment, components 22–32 can be included as part of an application specific integrated circuit (ASIC). More particularly, LED drive 22, conditioning circuit 24, modulators 26,28, RCAL drive 30 and modulator 32 are all configured as and produced as part of an ASIC, with modifications as needed for production on an ASIC. With this configuration, the major components of oximeter 10 would include probe 12, the ASIC, interface 20, CPU 34, the power supply and the display. This provides substantial advantages in terms of cost, size and power usage, and greatly simplifies inventory control, assembly and maintenance.

Figure 4A:
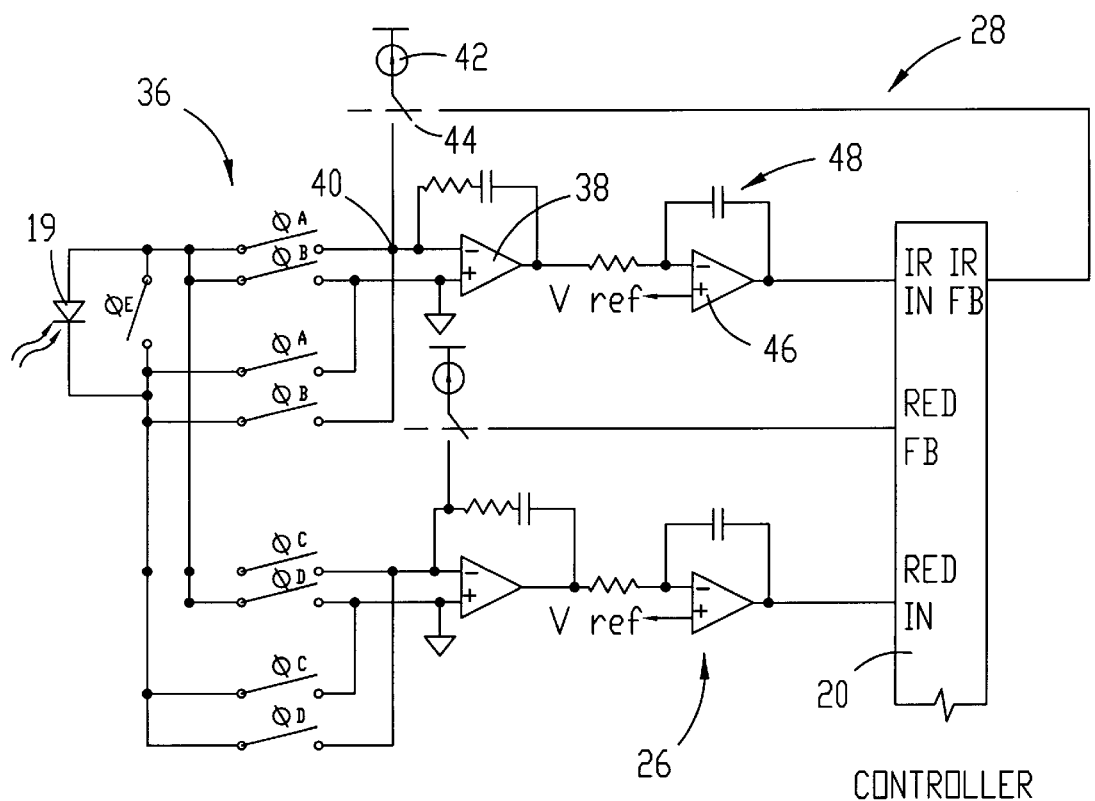
FIG. 4A is a simplified partial schematic of a preferred application specific integrated circuit for use in the oximeter of FIG. 1.
Figure 4B:
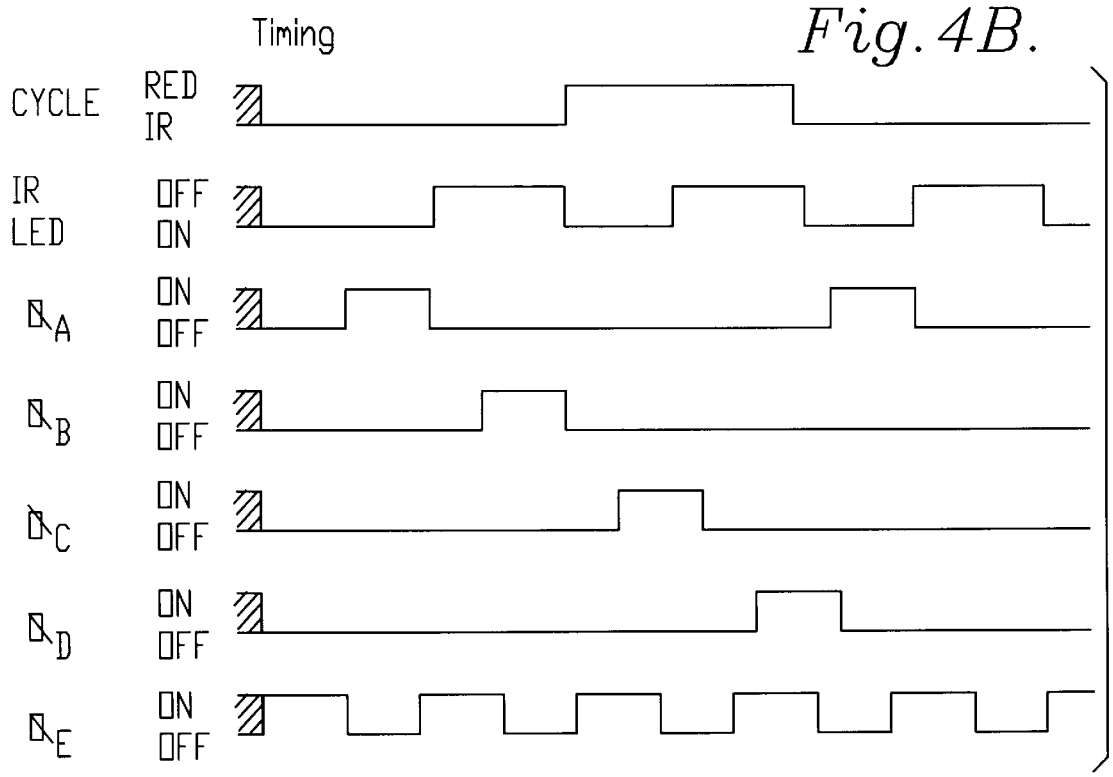
FIG. 4B is a timing diagram for the switches of FIG. 4A.

FIG. 4A is a simplified, partial schematic of the preferred ASIC 36 illustrating detector 19, red channel sigma-delta modulator 26, infrared channel sigma-delta modulator 28, interface 20 and switch pairs φA, φB, φC, φD and φE, operated under ASIC control. In this embodiment, signal conditioning circuit 24 is not used because other techniques available with ASICs are used for changing circuit gain. FIG. 4B is a timing diagram illustrating the operation of switches φA–E relative to the on/off cycles of LEDs 16,18.

As discussed above and illustrated in the first timing graph of FIG. 4B, the operation alternates between the infrared cycle and the red cycle. Each LED 16,18 is energized only during the first half of its cycle, i.e., the "on" portion, as illustrated in the second timing graph for infrared LED 18.

In the operation of the IR cycle, switches φA and φB are open during the first half of the on portion. (Third and fourth timing graphs.) Switches φA then close during the second half of the on portion of the IR cycle. When this occurs, detector 19 is connected between the noninverting and inverting terminals of operational amplifier (op amp) 38. Additionally, the anode of detector 19 is also connected to summing node 40, which is, in turn, connected to current source 42 by way of control switch 44 controlled by interface 20. Interface 20 operates control switch 44 with fixed width pulses in order to control the feedback to modulator 28. The number of closings of switch 44 represents the measure of current flow through detector 19.

Assuming control switch 44 is open initially, current flow through detector 19 drives the output voltage from op amp 38 to a negative value. This output is supplied to the inverting terminal of integrator 46 and results in a high level output from integrator 46, which is supplied to interface 20. In response to this high level output from integrator 46, interface 20 applies pulses to close switch 44. Each closure of switch 44 allows current source 42 to draw current from summing node 40 thereby driving the output of op amp 38 positive. This positive voltage is supplied to the inverting input of integrator 46. In time, in accordance with the value of capacitor 48, this positive input to integrator 46 will result in a lower output from integrator 46. Interface 20 continues to apply closing pulses to switch 44 at a rate sufficient to reduce the output from integrator 46 to a steady state balance (mid range). The pulse rate to switch 44 at the steady state condition represents the current flow through detector 19 and thereby represents the amount of transillumination of IR light through the subject's body portion.

The second half of the IR cycle is quiescent period in which IR LED is off. During the second portion of the off period, switches φB close. This connects detector 19 across the inputs to op amp 38, but with the cathode of detector 19 connected to the inverting input and to summing node 40. Interface 20 determines the current flow through detector 19 during this off period with switches φB closed. The current flow during this second portion of the off period represents ambient light and other sources and as used by interface 20 to compensate for these effects, that is, to zero the current readings.

The operation of red channel modulator 26 is the same as that of the IR channel modulator 28 except that it occurs during the red cycle using switches φC and φD. Switch φE is closed whenever switches φA–D are open. This shorts detector 19 and keeps the voltage at zero to prevent switch transients when switches φA–D make transition to the closed positions.

With an ASIC configuration, the gains through modulators 26,28 can be modified by adding and switching between additional current sources as a coarse adjustment and by changing the pulse width of the pulses to switch 44 as a fine adjustment. In addition, capacitors can be switched in and out to the circuit to change the response time of integrator 46.

In view of the preferred embodiments discussed above, those skilled in the art will now appreciate the many advantages of the present invention. These also include the ability for the circuit to adjust automatically the various gains without manual intervention. That is, the software in interface 20 automatically adjusts the gains within the sigma-delta converter itself. This ensures precision and accuracy over a wide range of detector signal levels.

Additionally, the integrated design of the ASIC also enables the use of low power supply voltages. Prior art oximeters use a current to voltage converter at the detector input which, for range and noise reasons, requires a large power supply voltage, typically +/−10 V. The preferred design eliminates the need for a current to voltage converter. Moreover, by using a ground sensing amplifier in the first integrator and biasing a second integrator to a reference voltage between ground and the positive supply (Vref), this design can operate on a single, low voltage supply such as +5 V or even +3.3 V.

The integrators shown in this design are representative of just one embodiment. Those skilled in the art will appreciate that the present invention encompasses other techniques for making integrators in an ASIC, such as switched capacitors and operational transconductance amplifiers.

The above discussion and related illustrations are directed primarily to preferred embodiments and practices of the invention. However, it is believed that numerous changes and modifications in the actual implementation of the concepts described will be apparent to those skilled in the art and it is contemplated that such changes and modifications may be made without departing from the scope of the invention as defined by the following claims.

What is claimed is:

1. An oximeter apparatus comprising:
   sensor means for producing first and second analog signals respectively representative of the transillumination of a body portion of an in vivo subject by respective first and second wavelengths of radiation;
   converter means for receiving and converting said first and second analog signals into respective first and second digital signals; and
   signal processing means for receiving and processing said first and second digital signals for determining blood oxygen saturation of the subject,
   said converter means including
      a first sigma-delta modulator for receiving said first analog signal and for producing a first sample signal representative thereof,
      a second sigma-delta modulator for receiving said second analog signal and for producing a second sample signal representative thereof, and
      a digital filter processor having means for receiving both of said first and second sample signals and responsive thereto for digitally filtering said sample signals in order to produce said respective first and second digital signals,
   said digital filter processor including programming for digitally filtering said sample signals in order to produce said first and second digital signals, and for controlling the input sampling rate from said modulators and controlling the filter corner frequency and output update rate of said first and second digital signals.

2. The apparatus as set forth in claim 1, said digital filter processor including means for successive decimation filtering of said sample signals.

3. The apparatus as set forth in claim 1, said digital filter processor including means for producing said first and second digital signals representative of said first and second analog signals with at least seventeen bit resolution respectively.

4. The apparatus as set forth in claim 1, said digital filter processor including a microprocessor.

5. The apparatus as set forth in claim 1, said modulators including over-sampling modulators.

6. The apparatus as set forth in claim 1, said modulators including second order modulators.

7. The apparatus as set forth in claim 1, said modulators including second order, over-sampling modulators, said digital filter processor including means for successive decimation filtering of said sample signals, said digital filter processor including means for producing said first and second digital signals representative of said first and second analog signals with at least seventeen bit resolution, said digital filter processor including a microprocessor.

8. The apparatus as set forth in claim 1, said digital filter processor including means for sampling at a rate of about 4.8 KHz and performing six stages of decimation filtering to produce an update rate of about 78 samples per second.

9. The apparatus as set forth in claim 1, said sensor means disposed in a probe having means for coupling said probe with said apparatus.

10. The apparatus as set forth in claim 1, said sensor means including a probe including
   first light emitting means for emitting light of said first wavelength having a first known wavelength value,
   light sensing means for sensing the light emitted by said first light emitting means, and
   encoding means for providing encoded signals indicative of at least said first known wavelength value.

11. The apparatus as set forth in claim 10 further including a second light emitting means for emitting light of said second wavelength having a second known wavelength value,
   said light sensing means including the means for sensing the light emitted from said second light emitting means,
   said encoding means including means for providing encoded signals indicative of at least said second known wavelength value.

12. The apparatus as set forth in claim 10, said encoding means including an electrical impedance element, the value of which is selected to correlate with said known wavelength value.

13. The apparatus as set forth in claim 12, said electrical impedance element including a resistor.

14. The apparatus as set forth in claim 13, said encoded signals including voltage signals produced by passing a current through said resistor.

15. The apparatus as set forth in claim 1, said sensor means including a non-invasive, electro-optical sensor probe configured for disposition onto a surface of the subject.

16. The apparatus as set forth in claim 15, said sensor probe being configured for flexibly conforming to the surface of the subject.

17. The apparatus as set forth in claim 15, said sensor probe being configured for removable disposition onto the surface of the subject.

18. The apparatus as set forth in claim 1, said wavelengths falling respectively in the infrared and red regions.

19. The apparatus as set forth in claim 1, said sensor means including first and second light emitting diodes for producing said first and second wavelengths of light, respectively.

20. The apparatus as set forth in claim 1, said converter means including gain adjusting means for adjusting the gains of said modulators in response to variations in said first and second analog signals.

21. The apparatus as set forth in claim 20, said adjusting means including programming within said digital filter processor for controlling the operation thereof.

22. The apparatus as set forth in claim 20, said converter means including signal amplifiers for amplifying said first and second analog signals, said gain adjusting means including means for adjusting the gain of said amplifiers.

23. The apparatus as set forth in claim 20, said converter means including means for providing feedback from said digital filter processor to said modulators, said gain adjusting means including feedback adjusting means for selectively adjusting said feedback in order to selectively adjust the gains of said modulators.

24. The apparatus as set forth in claim 23, said feedback adjusting means including programming in said digital filter processor for controlling the operation thereof.

25. An oximeter apparatus comprising:
sensor means for producing first and second analog signals respectively representative of the transillumination of a body portion of an in vivo subject by respective first and second wavelengths of radiation;
converter means for receiving and converting said first and second analog signals into respective first and second digital signals; and
signal processing means for receiving and processing said first and second digital signals for determining blood oxygen saturation of the subject,
said converter means including
a first sigma-delta modulator for receiving said first analog signal and for producing a first sample signal representative thereof,
a second sigma-delta modulator for receiving said second analog signal and for producing a second sample signal representative thereof, and
a digital filter processor having means for receiving both of said first and second sample signals and responsive thereto for digitally filtering said sample signals in order to produce said respective first and second digital signals,
said converter means including gain adjusting means for adjusting the gains of said modulators in response to variations in said first and second analog signals,
said adjusting means including programming within said digital filter processor,
said converter means including signal amplifiers for amplifying said first and second analog signals, said gain adjusting means including switching means for selectively switching resistance in connection with said amplifiers for adjusting the gains thereof.

26. The apparatus as set forth in claim 25, said adjusting means including programming within said digital processor operable for controlling said switching means.

27. An oximeter apparatus comprising:
sensor means for producing first and second analog signals respectively representative of the transillumination of a body portion of an in vivo subject by respective first and second wavelengths of radiation;
converter means for receiving and converting said first and second analog signals into respective first and second digital signals; and
signal processing means for receiving and processing said first and second digital signals for determining blood oxygen saturation of the subject,
said converter means including
a first sigma-delta modulator for receiving said first analog signal and for producing a first sample signal representative thereof,
a second sigma-delta modulator for receiving said second analog signal and for producing a second sample signal representative thereof, and
a digital filter processor having means for receiving both of said first and second sample signals and responsive thereto for digitally filtering said sample signals in order to produce said respective first and second digital signals,
said converter means including gain adjusting means for adjusting the gains of said modulators in response to variations in said first and second analog signals,
said first and second analog signals including respective first and second current signals, said converter means including means connecting said first and second current signals directly to amplifiers of said first and second sigma-delta modulators respectively without current to voltage conversion of said current signals.

28. The apparatus as set forth in claim 27, said converter means including gain adjusting means for adjusting the gains of said modulators in response to variations in said first and second analog signals.

29. The apparatus as set forth in claim 28, said converter means including feedback means for providing feedback signals in the nature of square waves having respective pulse widths as feedback from said digital filter processor to said modulators, said gain adjusting means including means for selectively adjusting said pulse widths in order to selectively adjust the gains of said modulators.

30. The apparatus as set forth in claim 29, said feedback means including programming in said digital filter processor for controlling the operation thereof.

31. The apparatus as set forth in claim 28, said converter means including current sources connected with said modulators in a configuration for interacting with said current signals, said gain adjusting means including means for selectively switching said current sources in order to adjust the gains of said modulators.

32. An oximeter apparatus comprising:
sensor means for producing first and second analog signals respectively representative of the transillumination of a body portion of an in vivo subject by respective first and second wavelengths of radiation:
converter means for receiving and converting said first and second analog signals into respective first and second digital signals; and
signal processing means for receiving and processing said first and second digital signals for determining blood oxygen saturation of the subject,
said converter means including
a first sigma-delta modulator for receiving said first analog signal and for producing a first sample signal representative thereof, a second sigma-delta modulator for receiving said second analog signal and for producing a second sample signal representative thereof, and a digital filter processor having means for receiving both of said first and second sample signals and responsive thereto for digitally filtering said sample signals in order to produce said respective first and second digital signals, said converter means including gain adjusting means for adjusting the gains of said modulators in response to variations in said first and second analog signals, said modulators including respective ground sensing amplifiers as first integrators and second integrators biased to a reference voltage between ground and supply voltage, said supply voltage being no greater than about +5 V.

33. An oximeter apparatus comprising:

sensor means for producing first and second analog signals respectively representative of the transillumination of a body portion of an in vivo subject by respective first and second wavelengths of radiation;

converter means for receiving and converting said first and second analog signals into respective first and second digital signals; and signal processing means for receiving and processing said first and second digital signals for determining a blood oxygen saturation of the subject, said converter means including
a first sigma-delta modulator for receiving said first analog signal and for producing a first sample signal representative thereof, a second sigma-delta modulator for receiving said second analog signal and for producing a second sample signal representative thereof, and a digital filter processor having means for receiving both of said first and second sample signals and responsive thereto for digitally filtering said sample signals in order to produce said respective first and second digital signals, said oximeter further including first and second light emitting diodes for producing said respective first and second wavelengths, a drive circuit for selectively activating said diodes, and deactivating means for determining the occurrence of a short circuit connected to said diodes and responsive thereto for deactivating said diodes.

34. An oximeter apparatus comprising:

sensor means for producing first and second analog signals respectively representative of the transillumination of a body portion of an in vivo subject by respective first and second wavelengths of radiation;

converter means for receiving and converting said first and second analog signals into respective first and second digital signals; and signal processing means for receiving and processing said first and second digital signals for determining blood oxygen saturation of the subject, said converter means including
a first sigma-delta modulator for receiving said first analog signal and for producing a first sample signal representative thereof, a second sigma-delta modulator for receiving said second analog signal and for producing a second sample signal representative thereof, and a digital filter processor having means for receiving both of said first and second sample signals and responsive thereto for digitally filtering said sample signals in order to produce said respective first and second digital signals, said sensor means including
a detachable probe configured for disposition onto a surface of a subject, said probe having first and second light emitting diodes for producing said first and second wavelengths of light respectively in the red and infrared bands and having a photo detector for producing said first and second analog signals, a drive circuit having means for selectively activating said diodes, and encoding means for providing analog encoded signals indicative of the wavelengths of light emitted by said diodes and including an impedance element included as part of said probe and operable for producing a voltage as said analog encoded signals, said apparatus further including a third sigma-delta modulator having means for receiving said analog encoded signals and for producing a third sample signal representative thereof, said digital signal filter processor having means for receiving said third sample signal and responsive thereto for digitally filtering said third sample signal for producing a digital encoded signal, said signal processing means including means for receiving and processing said digital encoded signal for use in calibrating said apparatus.

35. A method of determining the blood oxygen saturation of an in vivo subject comprising the steps of:

(a) producing first and second analog signals respectively representative of the transillumination of a body portion of the subject by respective first and second wavelengths of light;

(b) converting said first and second analog signals into respective first and second digital signals; and (c) processing said first and second digital signals for determining the blood oxygen saturation of the subject, step (b) further including the steps of
using a first sigma-delta modulator for receiving said first analog signal and for producing a first sample signal representative thereof, using a second sigma-delta modulator for receiving said second analog signal and for producing a second sample signal representative thereof, and providing both of said first and second sample signals to a digital filter processor and therein digitally filtering said sample signals in order to produce said respective first and second digital signals, step (b) further including the steps of using programming in said digital filter processor for digitally filtering said sample signals in order to produce said first and second digital signals, and for controlling the input sampling rate from said modulators and controlling the filter corner frequency and output update rate of said first and second digital signals.

36. The method as set forth in claim 35, step (b) including the step of using second order, over-sampling modulators as said modulators.

37. The method as set forth in claim 35, step (b) including the step of performing successive decimation filtering of said sample signals.

38. The method as set forth in claim 35, step (b) including the step of producing said first and second digital signals representative of said first and second analog signals with at least seventeen bit resolution.

39. The method as set forth in claim 35, step (b) including the step of using a microprocessor as said digital filter processor.

40. The method as set forth in claim 35, step (b) including the step of using over-sampling modulators as said modulators.

41. The method as set forth in claim 40, step (b) including the step of using second order modulators as said modulators.

42. The method as set forth in claim 35, step (b) including sampling at a rate of about 4.8 KHz and performing six stages of decimation filtering to produce an update rate of about 78 samples per second.

43. The method as set forth in claim 35, step (b) further including the step of adjusting the gains of said modulators in response to variations in said first and second analog signals.

44. The method as set forth in claim 43, step (b) further including the step of using programming within said digital filter processor for said adjusting.

45. The method as set forth in claim 43, step (b) further including the step of using amplifiers for amplifying said first and second analog signals and selectively adjusting the gain of said amplifiers.

46. A method of determining the blood oxygen saturation of an in vivo subject comprising the steps of:
   (a) producing first and second analog signals respectively representative of the transillumination of a body portion of the subject by respective first and second wavelengths of light;
   (b) converting said first and second analog signals into respective first and second digital signals; and
   (c) processing said first and second digital signals for determining the blood oxygen saturation of the subject,
   step (b) further including the steps of
      using a first sigma-delta modulator for receiving said first analog signal and for producing a first sample signal representative thereof,
      using a second sigma-delta modulator for receiving said second analog signal and for producing a second sample signal representative thereof, and
      providing both of said first and second sample signals to a digital filter processor and therein digitally filtering said sample signals in order to produce said respective first and second digital signals,
   step (b) further including the step of adjusting the gains of said modulators in response to variations in said first and second analog signals,
   step (b) further including the step of using amplifiers for amplifying said first and second analog signals and selectively adjusting the gain of said amplifiers, said method further including the step of selectively switching resistance in connection with said amplifiers for adjusting the gains thereof.

47. The method as set forth in claim 46, step (b) further including the step of using programming within said digital processor operable for controlling said switching.

48. A method of determining the blood oxygen saturation of an in vivo subject comprising the steps of:
   (a) producing first and second analog signals respectively representative of the transillumination of a body portion of the subject by respective first and second wavelengths of light;
   (b) converting said first and second analog signals into respective first and second digital signals; and
   (c) processing said first and second digital signals for determining the blood oxygen saturation of the subject,
   step (b) further including the steps of
      using a first sigma-delta modulator for receiving said first analog signal and for producing a first sample signal representative thereof,
      using a second sigma-delta modulator for receiving said second analog signal and for producing a second sample signal representative thereof, and
      providing both of said first and second sample signals to a digital filter processor and therein digitally filtering said sample signals in order to produce said respective first and second digital signals,
   step (b) further including the step of adjusting the gains of said modulators in response to variations in said first and second analog signals,
   step (b) further including the step of providing feedback from said digital filter processor to said modulators and adjusting said feedback in order to selectively adjust the gains of said modulators.

49. The method as set forth in claim 48, step (b) further including the step of using programming in said digital filter processor for adjusting said feedback.

50. A method of determining the blood oxygen saturation of an in vivo subject comprising the steps of:
   (a) producing first and second analog signals respectively representative of the transillumination of a body portion of the subject by respective first and second wavelengths of light;
   (b) converting said first and second analog signals into respective first and second digital signals; and
   (c) processing said first and second digital signals for determining the blood oxygen saturation of the subject,
   step (b) further including the steps of
      using a first sigma-delta modulator for receiving said first analog signal and for producing a first sample signal representative thereof,
      using a second sigma-delta modulator for receiving said second analog signal and for producing a second sample signal representative thereof, and
      providing both of said first and second sample signals to a digital filter processor and therein digitally filtering said sample signals in order to produce said respective first and second digital signals,
   step (b) further including the step of adjusting the gains of said modulators in response to variations in said first and second analog signals,
   said first and second analog signals including respective first and second current signals, step (b) further including the step of connecting said first and second current signals to amplifiers of said first and second sigma-delta modulators respectively without current to voltage conversion of said current signals.

51. The method as set forth in claim 50, step (b) further including the step of using current sources connected with said modulators in a configuration for interacting with said current signals and selectively switching said current sources in order to adjust the gains of said modulators.

52. The method as set forth in claim 50, said modulators including respective ground sensing amplifiers as first integrators and second integrators biased to a reference voltage between ground and supply voltage, step (b) further including the step of providing said supply voltage no greater than about +5 V.

53. A method of determining the blood oxygen saturation of an in vivo subject comprising the steps of:

(a producing first and second analog signals respectively representative of the transillumination of a body portion of the subject by respective first and second wavelengths of light;

(b converting said first and second analog signals into respective first and second digital signals; and (c) processing said first and second digital signals for determining the blood oxygen saturation of the subject, step (b) further including the steps of
using a first sigma-delta modulator for receiving said first analog signal and for producing a first sample signal representative thereof,
using a second sigma-delta modulator for receiving said second analog signal and for producing a second sample signal representative thereof, and
providing both of said first and second sample signals to a digital filter processor and therein digitally filtering said sample signals in order to produce said respective first and second digital signals, step (b) further including the step of adjusting the gains of said modulators in response to variations in said first and second analog signals, step (b) further including the step of providing feedback signals in the nature of square waves having respective pulse widths as feedback from said digital filter processor to said modulators, and selectively adjusting said pulse widths in order to selectively adjust the gains of said modulators.

54. The method as set forth in claim 53, step (b) further including the step of using programming in said digital filter processor for controlling said pulse widths.

55. A method of determining the blood oxygen saturation of an in vivo subject comprising the steps of:

(a) producing first and second analog signals respectively representative of the transillumination of a body portion of the subject by respective first and second wavelengths of light;

(b) converting said first and second analog signals into respective first and second digital signals; and (c) processing said first and second digital signals for determining the blood oxygen saturation of the subject, step (b) further including the steps of
using a first sigma-delta modulator for receiving said first analog signal and for producing a first sample signal representative thereof,
using a second sigma-delta modulator for receiving said second analog signal and for producing a second sample signal representative thereof, and
providing both of said first and second sample signals to a digital filter processor and therein digitally filtering said sample signals in order to produce said respective first and second digital signals, step (b) further including the step of adjusting the gains of said modulators in response to variations in said first and second analog signals, step (b) further including the steps of using first and second light emitting diodes for producing said respective first and second wavelengths, using a drive circuit for selectively activating said diodes, and determining the occurrence of a short circuit connected to said diodes and responsive thereto for deactivating said diodes.

* * * * *